(12) United States Patent
Burton et al.

(10) Patent No.: US 9,275,842 B2
(45) Date of Patent: Mar. 1, 2016

(54) MULTI-DOPANT PERMEATION TUBE

(75) Inventors: Timothy B. Burton, Danville, NH (US); Stephen Scott Milt, Winchester, MA (US)

(73) Assignee: DSA DETECTION LLC, North Andover, MA (US)

( * ) Notice: Subject to any disclaimer, the term of this patent is extended or adjusted under 35 U.S.C. 154(b) by 118 days.

(21) Appl. No.: 13/698,507

(22) PCT Filed: May 22, 2012

(86) PCT No.: PCT/US2012/038996
§ 371 (c)(1), (2), (4) Date: Nov. 16, 2012

(87) PCT Pub. No.: WO2012/166439
PCT Pub. Date: Dec. 6, 2012

(65) Prior Publication Data
US 2013/0140455 A1 Jun. 6, 2013

Related U.S. Application Data

(60) Provisional application No. 61/490,701, filed on May 27, 2011.

(51) Int. Cl.
*H01J 49/00* (2006.01)
*H01J 49/04* (2006.01)
*G01N 27/62* (2006.01)

(52) U.S. Cl.
CPC .......... *H01J 49/0422* (2013.01); *G01N 27/622* (2013.01)

(58) Field of Classification Search
CPC ...................................................... H01J 49/00
USPC ......................................... 250/281, 282, 288
See application file for complete search history.

(56) References Cited

U.S. PATENT DOCUMENTS

| | | | | |
|---|---|---|---|---|
| 3,650,042 A | * | 3/1972 | Boerger et al. | 34/611 |
| 5,191,211 A | * | 3/1993 | Gorman, Jr. | 250/282 |
| 5,283,199 A | * | 2/1994 | Bacon et al. | 436/173 |
| 5,365,873 A | * | 11/1994 | Wigram | 114/367 |
| 5,968,837 A | * | 10/1999 | Doring et al. | 436/173 |
| 6,495,824 B1 | * | 12/2002 | Atkinson | 250/287 |
| 2002/0121596 A1 | | 9/2002 | Laiko et al. | |
| 2004/0159784 A1 | | 8/2004 | Doroshenko et al. | |
| 2004/0235193 A1 | * | 11/2004 | Soldin | 436/518 |

(Continued)

FOREIGN PATENT DOCUMENTS

WO  WO 2006129101 A1  * 12/2006

OTHER PUBLICATIONS

Daum et al., "Resolving Interferences in Negative Mode Ion Mobility Spectrometry Using Selective Reactant Ion Chemistry", Talanta 54 (2001) 299-306.

*Primary Examiner* — Nicole Ippolito
*Assistant Examiner* — Jason McCormack
(74) *Attorney, Agent, or Firm* — Lando & Anastasi, LLP

(57) ABSTRACT

Aspects and embodiments of the present invention are directed to spectrometry systems and for apparatus and methods for delivering dopants to same. In one example, there is provided a dopant delivery device configured to supply dopants to a spectrometry system comprising a tube including a first chamber and a second chamber, a first dopant source included in the first chamber, and a second dopant source included in the second chamber.

25 Claims, 3 Drawing Sheets

(56) References Cited

U.S. PATENT DOCUMENTS

| | | |
|---|---|---|
| 2005/0016984 A1 | 1/2005 | Dando |
| 2005/0070848 A1 | 3/2005 | Kim et al. |
| 2006/0144140 A1* | 7/2006 | Hache .............................. 73/295 |
| 2006/0219892 A1* | 10/2006 | Walte et al. .................. 250/288 |
| 2006/0249673 A1* | 11/2006 | Breach et al. ................. 250/292 |
| 2008/0166792 A1 | 7/2008 | Attar et al. |
| 2008/0193962 A1 | 8/2008 | Wada et al. |
| 2009/0174412 A1* | 7/2009 | Atkinson et al. ............ 324/469 |
| 2009/0179146 A1* | 7/2009 | Lomas et al. ................ 250/282 |
| 2009/0255351 A1* | 10/2009 | Stearns et al. ............. 73/864.81 |
| 2009/0294649 A1 | 12/2009 | Shabanowitz et al. |
| 2009/0303295 A1* | 12/2009 | Silverbrook et al. ........... 347/85 |
| 2010/0223979 A1* | 9/2010 | Ploehn et al. ...................... 73/38 |
| 2010/0262074 A1* | 10/2010 | Seiferlein et al. ............... 604/89 |
| 2010/0282077 A1 | 11/2010 | Jones et al. |
| 2010/0282962 A1* | 11/2010 | Machuron-Mandard et al. ............................. 250/282 |
| 2010/0308216 A1* | 12/2010 | Clark et al. .................... 250/282 |
| 2011/0133076 A1* | 6/2011 | Miller et al. ................... 250/287 |
| 2011/0266433 A1* | 11/2011 | Jarrell ............................ 250/282 |

\* cited by examiner

MULTI-DOPANT PERMEATION TUBE

RELATED APPLICATIONS

This application is a US National Stage Application under 35 U.S.C. §371 from PCT/US2012/038996, filed May 22, 2012, which claims priority under 35 U.S.C. §119(e) to U.S. Provisional Application Ser. No. 61/490,701, titled "MULTI-DOPANT PERMEATION TUBE," filed on May 27, 2011, which is herein incorporated by reference in its entirety.

BACKGROUND

1. Field of Disclosure

Aspects and embodiments of the present disclosure are directed to spectrometry systems and for apparatus and methods for delivering dopants to same.

2. Discussion of Related Art

Ion mobility spectrometers (IMS) and ion trap mobility spectrometers (ITMS) are used to detect and identify trace amounts of airborne chemicals. These types of spectrometers are sometimes employed to detect explosives or narcotics Ammonia and dichloromethane (DCM) are used as dopants that enable the transport of sampled materials within an IMS or ITMS spectrometer. These dopants are used to accept a transfer of charge created during ionization of a carrier gas used to carry a sample through the spectrometer. Ionization of the carrier gas is thus reduced, reducing the amount of spectrometer detector readings that might otherwise occur due to ionized carrier gas and increasing the signal to noise ratio of the spectrometer. A dopant may be introduced to a carrier gas by flowing the carrier gas around a permeation tube which releases a controlled concentration of a dopant into the carrier gas. In the current state of the art, a spectrometer uses two separate permeation tubes to convey the ammonia gas (positive ion dopant) and DCM (negative ion dopant) inside the spectrometer.

SUMMARY

Aspects and embodiments of the present disclosure include a device used for introduction of dopants, for example, ammonia and dichloromethane (DCM), into a spectrometry system, such as an ion mobility spectrometer or ion trap mobility spectrometer and to spectrometry systems including such devices.

In accordance with an aspect of the present disclosure there is provided a dopant delivery device configured to supply dopants to a spectrometry system. The dopant delivery device comprises a tube including a first chamber and a second chamber, a first dopant source included in the first chamber, and a second dopant to source included in the second chamber.

In accordance with some embodiments, the first chamber is defined by a wall of the tube, a first plug inserted into a portion of the tube proximate a first end of the tube, and by a second plug inserted into the tube at a position remote from the first end of the tube. In some embodiments, the second chamber is defined by the wall of the tube, a third plug inserted into a portion of the tube proximate a second end of the tube, and by the second plug. In some embodiments, a bore is defined in one of the first plug and the third plug.

In accordance with some embodiments, the first dopant source comprises dichloromethane liquid. In accordance with some embodiments, the wall of the tube defining one of the first chamber and the second chamber is permeable to dichloromethane vapor. In accordance with some embodiments, the second dopant source comprises an ammonia solid.

In accordance with some embodiments, the dopant delivery device is configured to emit both dichloromethane vapor and ammonia vapor.

In accordance with some embodiments, the dopant delivery device is configured to provide a visual indication of the expiration of the supply of the first dopant source and of the expiration of the supply of the second dopant source. In some embodiments, the visual indication includes a visual indication of a fluid level of the dichloromethane liquid. In some embodiments, the visual indication includes a visual indication of a color of an indicator material.

In accordance with some embodiments, the dopant delivery device is coupled to the spectrometry system.

In accordance with another aspect of the present disclosure, there is provided a method of supplying a plurality of dopants to a spectrometry system. The method comprises loading a first quantity of a first dopant into a first chamber of a dual-mode dopant tube, a remaining quantity of the first dopant visually ascertainable through a wall of the first chamber, loading a second quantity of a second dopant into a second chamber of the dual mode-dopant tube, the second quantity of the second dopant having an expected time for depletion greater than an expected time for depletion of to the first quantity of the first dopant, loading the dual-mode dopant tube into a dopant tube port of the spectrometry system, and heating the dual-mode dopant tube, resulting in the release of a portion of the first dopant and a portion of the second dopant from the dual-mode dopant tube and in to the spectrometry system.

In accordance with another aspect of the present disclosure, there is provided an apparatus configured to supply dopants to a spectrometry system. The apparatus comprises a first chamber coupled to a second chamber. The first chamber is configured to retain a first dopant source and to release a first dopant from the first dopant source from an internal volume of the first chamber. The second chamber is configured to retain a second dopant source and to release a second dopant from the second dopant source from an internal volume of the second chamber.

In accordance with some embodiments, the first chamber includes a wall contiguous with a wall of the second chamber.

In accordance with some embodiments, a wall of the first chamber is formed of a material different from a material of which the second chamber is formed.

In accordance with some embodiments, the first chamber has a dimension which differs from a corresponding dimension of the second chamber.

In accordance with some embodiments, the apparatus is configured to be mounted in a port of the spectrometry system and to deliver the first dopant and the second dopant into the spectrometry system from within the port.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
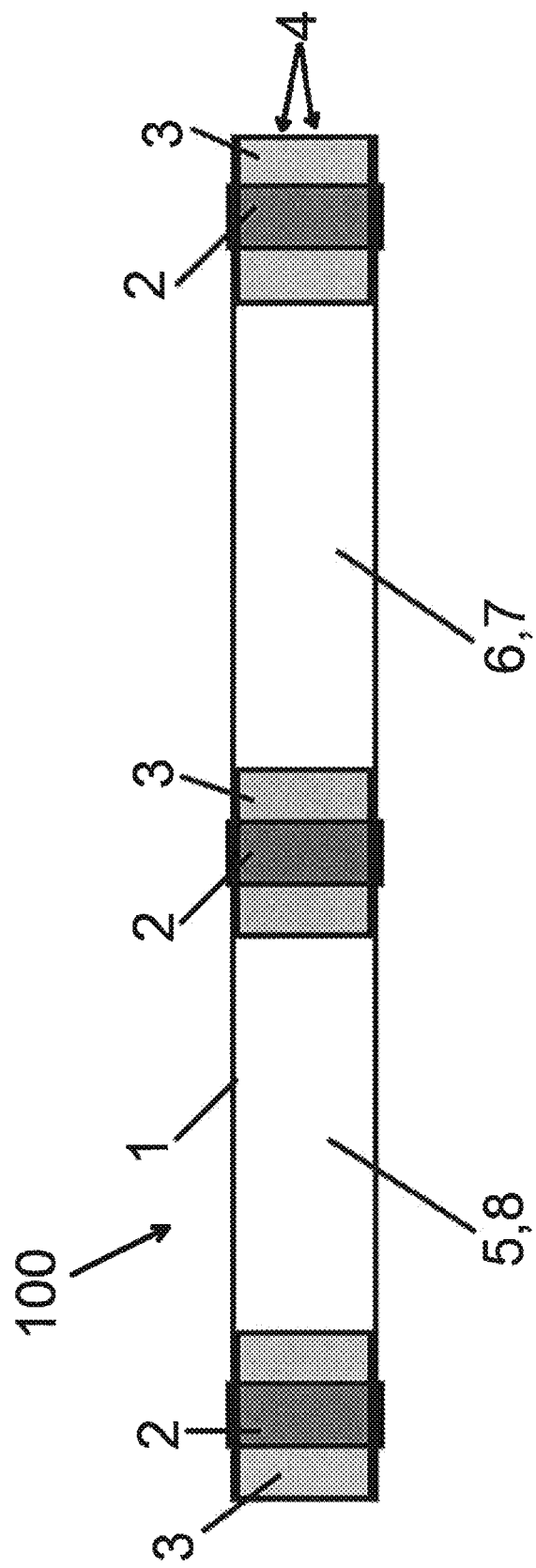
FIG. 1 is a side view of a dopant delivery device in accordance with an embodiment of the present disclosure.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

An embodiment of a dopant delivery device in accordance with the present disclosure is illustrated in FIG. 1, indicated generally at 100. This device may be referred to as a dual-mode dopant tube. The device includes a tube 1. In some embodiments, the tube is formed from a material, such as polytetrafluoroethylene (PTFE), which is permeable to certain dopants, such as dichloromethane. In some embodiments, the tube wall is formed of a solid, non-porous material, and in other embodiments, the tube may include one or more pores or apertures on at least a portion of the tube wall. In some embodiments, the tube 1 is visually transparent or translucent. In one embodiment, the tube 1 has a diameter of about 0.5 inches (about 1.27 cm) and a thickness of about 0.03 inches (about 0.076 cm), and is divided into two one-inch long chambers 5, 6, although the tube may be sized to accommodate or adapt to different spectrometry systems. A tube formed of PTFE and having a length of one inch (2.54 cm), a diameter of 0.5 inches (1.27 m), and a wall thickness of 0.03 inches (0.076 cm) will permeate dichloromethane at a rate of about 4,600±460 nanograms per minute (ng/min) at a temperature of 30° Celsius at atmospheric pressure. Different materials, dimensions and/or thicknesses of the tube 1 could be utilized to achieve a desired permeation rate of dichloromethane. In some embodiments, the tube 1 may include markings, for example, score marks, which may provide an indication to a user of an amount of dopant present in the tube. For to example, each score mark may indicate a specific volume of the tube. A user may fill the tube with a dopant until the volume of the dopant reaches a score mark indicating a desired quantity of dopant. A user may periodically check the quantity of a dopant which is visibly discernable through the wall of the tube by checking the level of the dopant against the score marks on the tube. For dopants which are not visibly discernable through the wall of the tube 1, a user may remove a plug 3 enclosing the dopant in the dopant chamber to check the amount of remaining dopant remaining therein.

The tube 1 is separated into two chambers, a first chamber 5 and a second chamber 6, separated by a plug 3 which may be secured in place by a collar 2. Additional plugs 3 may seal the ends of the tube 1. The plugs 3 may be formed as short rods having a diameter approximately equal to the inside diameter of the tube 1, or in some embodiments, from about 5% to about 10% greater than the inside diameter of the tube 1. The plugs 3 may be formed from a material such as virgin PTFE or one or more other resilient materials which may be chemically resistant to dopant sources which are to be used in the dopant delivery device. The plugs 3 may provide an interference fit inside the tube 1. Collars 2 may exert a compressive force on the outside surface of the tube 1 and facilitate securing the plugs 3 in place within the tube 1. The plugs 3, alone or in combination with the collars 2, may seal the various sections of the tube, thereby preventing leakage of gas or liquid from the chambers of the tube 1 and/or preventing cross contamination between the sealed chambers 5, 6 of the tube 1.

Figure 2:
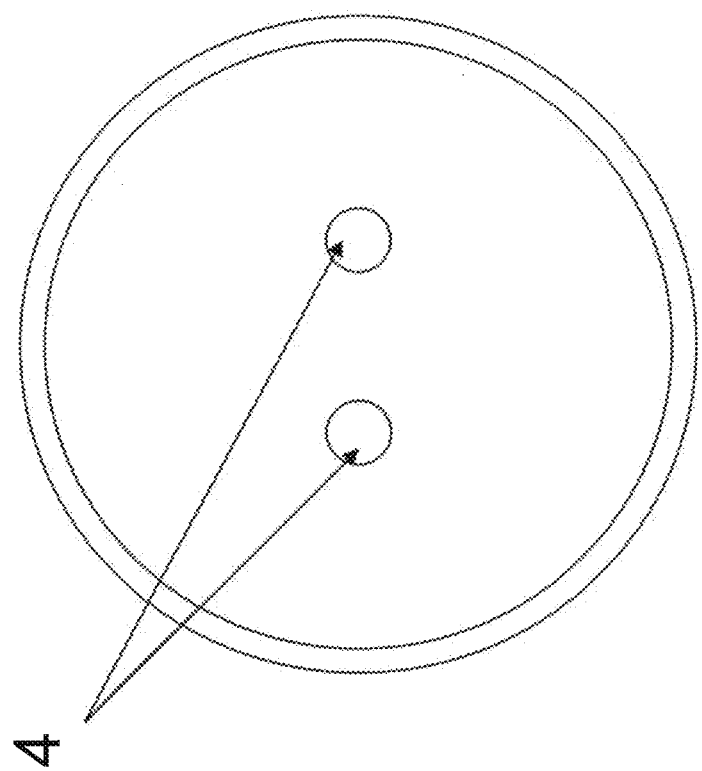
FIG. 2 is an end view of the device of FIG. 1.

The plug 3 at the outside end of the chamber 6 may include one or more bores 4 (illustrated in FIG. 2) formed in the plug 3. The bores may provide for the controlled release of a dopant from the second chamber 6, which is incapable of permeating the walls of the tube 1. For example, anhydrous ammonium carbamate powder 7 may be placed in the second chamber 6 to produce ammonia gas when heated to, for example, a temperature of about 30° Celsius. The ammonia gas may exit the second chamber 6 through the bores 4. The provision of two bores 4, each with a diameter of about $\frac{1}{32}$ of an inch (about 0.079 cm), with a total opening surface area of $1.53 \times 10^{-3}$ inches$^2$ (about $9.87 \times 10^{-3}$ cm$^2$), will provide for permeation to of ammonia gas from the second chamber 6 at a rate of about 9,000±900 ng/min. Different bore sizes and/or different numbers of bores could provide for different permeation rates as desired. Other ammonia producing compounds may be utilized in addition to, or in place of the anhydrous ammonium carbamate powder 7. Additional and/or other chemical sources may be present in the second chamber 6 to provide additional and/or different dopants.

In some embodiments, one or more pores or apertures may be provided in the wall of the first chamber 5 and/or the second chamber 6 to allow for the permeation of dopant gas therethrough. In some embodiments, dopants placed in each of the first chamber 5 and the second chamber 6 may produce gasses capable of permeating through the material of the walls of the tube and no bores, pores, or apertures would be needed in either of the first chamber 5 or the second chamber 6.

In use, the first chamber 5 may be partially filled with a quantity of dichloromethane 8 or some other dopant source, while the second chamber 6 is at least partially filled with a quantity of anhydrous ammonium carbamate powder or other dopant source. The dopant source used in chamber 5 may in some embodiments be dichloromethane with a purity of about 99.8% or above, mixed with amylene. The dopant source in chamber 5 may provide negative ion dopants for use in an IMS or ITMS detector, while the dopant source in chamber 6 may provide a positive ion dopant for use in an IMS or ITMS detector.

In some embodiments, the amount of a first dopant source whose depletion may readily be gauged by observation, for example, by visual observation through a wall of the tube 1, may be included in one of chambers 5 or 6 while a second dopant source whose depletion may not be readily gauged by observation may be included in the other one of the chambers 5 or 6. The amount of the dopants added to the chambers may be calibrated such that the dopant source whose depletion may readily be gauged by observation is provided in a quantity such that this dopant will be depleted prior to the depletion of the dopant source whose depletion may not be readily be gauged by observation. For example, in the first chamber 5, dichloromethane may be provided as a liquid, a level of which may be visually ascertained through the wall of the tube 1. In the second chamber 6, ammonium to carbamate powder may be provided. During use, the ammonium carbamate powder may decompose and coat the inside of the tube 1, or a residual amount of ammonium carbamate powder may be left on the inside of the tube 1, thus obscuring an accurate visual reading of the remaining amount. An amount of ammonium carbamate may be loaded into the chamber 6 that exceeds the lifetime of the dichloromethane liquid loaded into the chamber 5, so that the limiter of the useful lifetime of the dopant delivery device comprising the tube 1 is the dichloromethane. This allows the user to quickly ascertain the remaining useful lifetime of the dopant delivery device by observing the dichloromethane side of the tube 1 only.

In some embodiments, one or more additional mechanisms for determining a remaining useful lifetime or the presence of one or more dopants in the first chamber 5 and/or the second chamber 6 may be provided. For example, a portion of the wall of the tube 1 may be coated or surrounded with an indicator material which reacts by, for example, changing color in the presence of a particular dopant or a gaseous form of a particular dopant. Alternatively or additionally, a color changing strip including the color changing indicator material may be included in one of the chambers of the tube 1. The color of the indicator material may change when the dopant has become depleted, providing for a user to visibly ascertain if a dopant to which the color changing indicator material reacts remains in the tube 1 or not. In other embodiments, a time-sensitive indicator material which changes color over time in the presence of a particular dopant may be provided in one of the chambers of the tube 1 or on or surrounding a wall of the tube 1. An amount of dopant may be added to the tube 1 which would expect to become depleted in a time corresponding to the time it would take the time-sensitive indicator material to change color. The color of the time-sensitive indicator material may change when the dopant has become depleted, providing for a user to visibly ascertain if a dopant to which the time-sensitive indicator material reacts remains in the tube 1 or not.

In some embodiments, the tube 1 may be provided with a single chamber into which a plurality of dopant sources may be added, at least one of which having a volume which may be ascertained, visually or otherwise, through the wall of the tube 1. In such embodiments, the plurality of dopant sources may be compatible, for example, not reacting with one another or inhibiting the production of dopants from one another.

In further embodiments, the two chambers 5, 6 may be formed from different tubes and joined together. The material(s) of which the tubes defining the chambers 5, 6 may be the same, or in other embodiments, different. For example, one of the tubes defining one of the chambers 5, 6 may be formed from PTFE while the other tube is formed from a different polymer, for example, perfluoroalkoxy (PFA), fluorinated ethylene-propylene (FEP), or polyvinylidene fluoride (PVDF). In some embodiments, one or more dimensions, for example a wall thickness, length, or diameter of one of the chambers 5, 6, may differ from one or more dimensions of another of the chambers 5, 6. In some embodiments, one or both of the tubes defining the chambers 5, 6 may have solid, non-porous walls, and in other embodiments, one or both of the tubes defining the chambers 5, 6 may have porous walls. In further embodiments, the chambers 5, 6, are not limited to being tubes, but may have any suitable shape conducive to the storage of one or more dopant sources and the release of one or more dopants.

Figure 3:
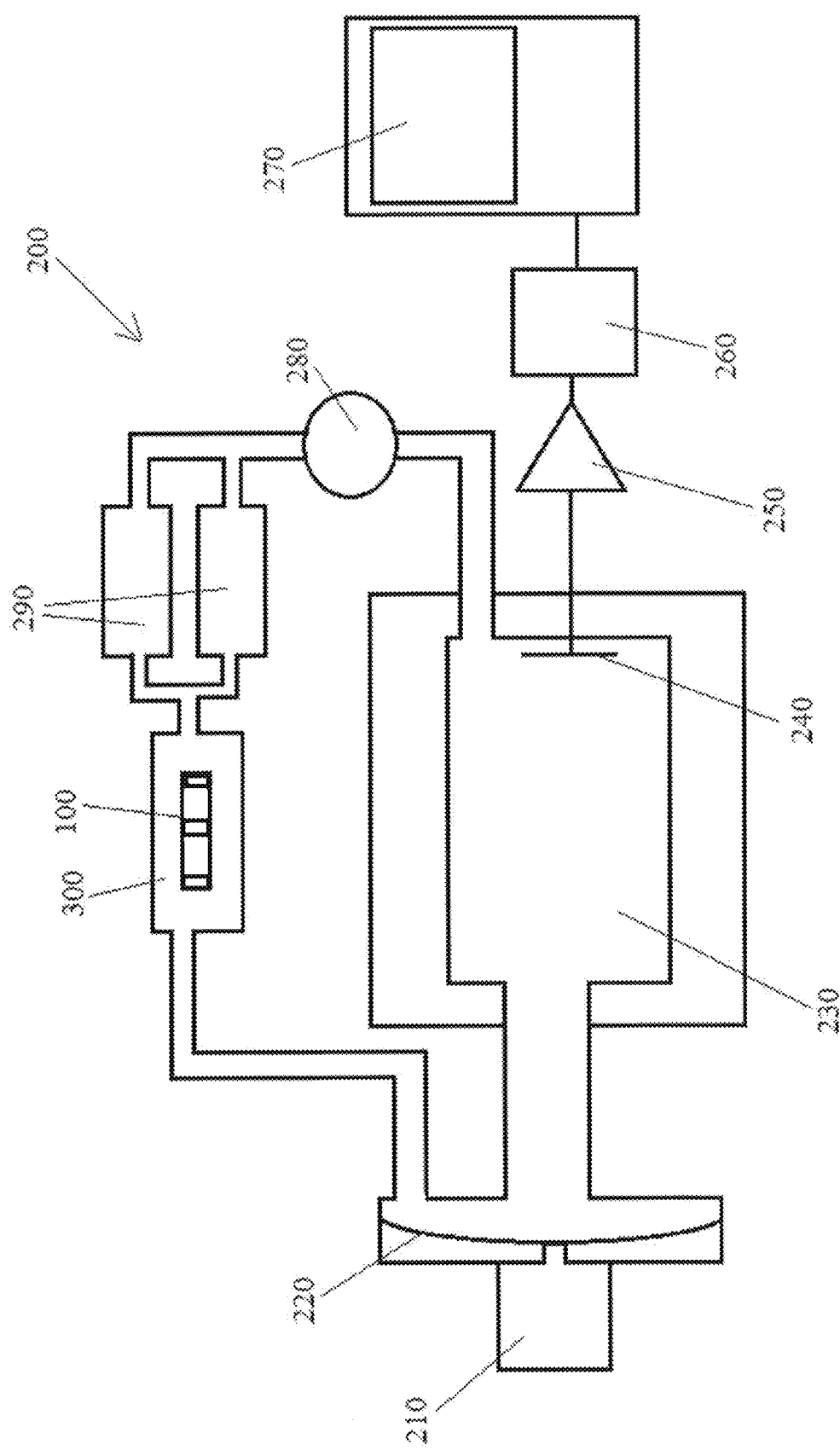
FIG. 3 is a schematic illustration of the dopant delivery device of FIG. 1 coupled to a spectrometry system.

In further embodiments, as illustrated in FIG. 3, the dopant introduction apparatus 100 is coupled to, or mounted within an IMS or ITMS detector 200. Samples are collected with sampling media, such as sample traps or sample swabs made of PTFE-coated fiberglass, paper, cloth, polyimide, or NOMEX® meta-aramid material may be vaporized in the desorber 210. The vaporized molecules then may pass through a semi-permeable membrane 220 and into the detector. In an analysis chamber 230 of the spectrometer the vaporized molecules are ionized so that they can be mobilized through the detector by an electric field. The time of flight which is the length of time it takes a substance to pass through the detector, depends on the mobility of the ion, and hence the species of the ion. Ions are detected as they hit the collector 240. The detection events are processed through a pre-amplifier 250 and a signal processor 260, and the resultant data displayed on a display 270, for example, a computer monitor. A carrier gas present in the analysis chamber is circulated by a pump 280 through one or more drying units 290 and a dopant chamber 300. The dopant delivery device 100 is present in the dopant chamber 300, for example, in a to dopant tube port. The dopant delivery device 100 introduces dopants into the carrier gas as the carrier gas circulates through the apparatus. The dopant delivery device 100 may introduce dopants into the carrier gas upon heating of the dopant delivery device to, for example, a temperature of about 30° Celsius. One or more dopants may be introduced into the carrier gas by permeating through a wall in a first and/or a second chamber of the dopant delivery device 100. One or more dopants may be introduced into the carrier gas by passing through a bore, aperture, or pore in a wall of the first and/or the second chamber of the dopant delivery device 100.

In accordance with further aspects of the present disclosure, there is provided a method of supplying dopants to a spectrometry system, for example, an IMS or an ITMS system. Embodiments of the method may include providing a dual-mode dopant tube such as that illustrated in FIG. 1 and FIG. 2, or as otherwise described above. A first quantity of a first dopant, for example DCM, may be loaded into a first chamber of a dual-mode dopant tube. In some embodiments, the quantity of the first dopant is visually ascertainable through a wall of the first chamber. The first quantity of the first dopant may be measured out prior to the addition of the dopant to the tube, or may be determined during the loading of the dopant by, for example, comparing a level of the dopant in the tube to markings on the tube, when present. Embodiments of the method may further include loading a second quantity of a second dopant, for example, ammonium carbamate, into a second chamber of the dual mode-dopant tube. In some embodiments, the second quantity of the second dopant may be measured out, either prior to or during loading of the second dopant into the second chamber, such that an amount of the second dopant is loaded which has an expected time for depletion greater than an expected time for depletion of the first quantity of the first dopant. The dual-mode dopant tube may then be loaded into a dopant tube port of the spectrometry system for use. The remaining quantity of one or both of the dopants may periodically be checked by a user. In some embodiments checking the remaining quantity of the first and/or second dopant may include visually ascertaining a remaining quantity of the first and/or second dopant through a wall of the tube 1. In some embodiments, if a useful remaining quantity of one of the dopants is observed, this may serve as an indication that a useful remaining quantity of the other dopant to also remains.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:
1. A dopant delivery device configured to supply dopants to a spectrometry system, the dopant delivery device comprising:
 a tube including a first chamber and a second chamber, wherein the first chamber is defined by a wall of the tube, a first plug located within a portion of the tube proximate a first end of the tube, and by a second plug located within a portion of the tube at a position remote from the first end of the tube and remote from a second end of the tube;

a first dopant source included in the first chamber; and a second dopant source included in the second chamber, the dopant delivery device configured to be disposed within a dopant chamber of the spectrometry system and to introduce the first dopant and the second dopant into a carrier gas in the dopant chamber.

2. The dopant delivery device of claim 1, wherein the second chamber is defined by the wall of the tube and a third plug inserted into a portion of the tube proximate the second end of the tube.

3. The dopant delivery device of claim 2, wherein a bore is defined in one of the first plug and the third plug.

4. The dopant delivery device of claim 1, wherein the first dopant source comprises dichloromethane liquid.

5. The dopant delivery device of claim 4, wherein the wall of the tube defining the first chamber is permeable to dichloromethane vapor.

6. The dopant delivery device of claim 1, wherein the second dopant source comprises an ammonia solid.

7. The dopant delivery device of claim 6, configured to emit both dichloromethane vapor and ammonia vapor.

8. The dopant delivery device of claim 1, configured to provide a visual indication of an expiration of the supply of either the first dopant source or the second dopant source.

9. The dopant delivery device of claim 8, wherein the visual indication includes a visual indication of a fluid level of dichloromethane liquid.

10. The dopant delivery device of claim 8, wherein the visual indication includes a visual indication of a color of an indicator material.

11. The dopant delivery device of claim 1, coupled to the spectrometry system.

12. A method of utilizing a dopant delivery device configured to supply dopants to a spectrometry system from within a dopant chamber of the spectrometry system, the method comprising: loading a first quantity of a first dopant into a first chamber of a tube, wherein the tube includes the first chamber defined by a wall of the tube, a first plug located within a portion of the tube proximate a first a first end of the tube, and by a second plug located within the tube at a position remote from the first end of the tube and remote from a second end of the tube; and loading a second quantity of a second dopant into a second chamber of the tube.

13. An apparatus configured to supply dopants to a spectrometry system from within a dopant chamber of the spectrometry system, the apparatus comprising:

a first chamber coupled to a second chamber wherein the first chamber includes a wall contiguous with a wall of the second chamber;

the first chamber configured to retain a first dopant source and to release a first dopant from the first dopant source from an internal volume of the first chamber into a carrier gas in the dopant chamber; and the second chamber configured to retain a second dopant source and to release a second dopant from the second dopant source from an internal volume of the second chamber into the carrier gas in the dopant chamber.

14. The apparatus of claim 13, wherein the first chamber has a dimension which differs from a corresponding dimension of the second chamber.

15. The apparatus of claim 13, configured to be mounted in a port of the spectrometry system and to deliver the first dopant and the second dopant into the spectrometry system from within the port.

16. An apparatus configured to supply dopants to a spectrometry system from within a dopant chamber of the spectrometry system, the apparatus comprising:

a first chamber coupled to a second chamber, wherein a wall of the first chamber is formed of a material different from a material of which the second chamber is formed;

the first chamber configured to retain a first dopant source and to release a first dopant from the first dopant source from an internal volume of the first chamber into a carrier gas in the dopant chamber; and the second chamber configured to retain a second dopant source and to release a second dopant from the second dopant source from an internal volume of the second chamber into the carrier gas in the dopant chamber.

17. The dopant delivery device of claim 1, wherein one of the first plug and the second plug are secured in place within the tube by a collar which exerts a compressive force on an outside surface of the tube.

18. The dopant delivery device of claim 1, wherein a portion of the wall of the tube is porous.

19. The dopant delivery device of claim 1, further comprising an indicator material which changes color in the presence of either the first dopant or the second dopant.

20. The dopant delivery device of claim 1, wherein the first chamber includes a wall contiguous with a wall of the second chamber.

21. The dopant delivery device of claim 1, wherein the first plug and the second plug provide interference fits inside the tube.

22. The dopant delivery device of claim 1, wherein the second plug seals the first chamber from the second chamber.

23. The dopant delivery device of claim 1, wherein the second plug comprises a rod having a diameter approximately equal to an inside diameter of the tube.

24. The dopant delivery device of claim 22, wherein the second plug prevents leakage of gas between the first chamber and the second chamber and prevents cross contamination between the first chamber and the second chamber.

25. The dopant delivery device of claim 1, wherein the wall of the tube is solid and non-porous and includes no apertures.

* * * * *

UNITED STATES PATENT AND TRADEMARK OFFICE
CERTIFICATE OF CORRECTION

PATENT NO. : 9,275,842 B2  
APPLICATION NO. : 13/698507  
DATED : March 1, 2016  
INVENTOR(S) : Timothy B. Burton et al.

Page 1 of 1

It is certified that error appears in the above-identified patent and that said Letters Patent is hereby corrected as shown below:

In the Specification:

Column 1, line number 53, delete "to".
Column 2, line number 26, delete "to".
Column 3, line number 40, delete "to".
Column 4, line number 13, delete "to".
Column 4, line number 55, delete "to".
Column 6, line number 6, delete "to".
Column 6, line number 50, delete "to".

In the Claims:

Column 7, claim 12, line number 42, delete "a first" between "proximate" and "a".

Signed and Sealed this
Twenty-sixth Day of July, 2016

Michelle K. Lee
*Director of the United States Patent and Trademark Office*